US012706183B2

(12) United States Patent
Valente

(10) Patent No.: US 12,706,183 B2
(45) Date of Patent: Aug. 11, 2026

(54) MIGRAINE SYMPTOM AND MEDICATION TRACKING DEVICE FOR USE IN SYSTEMS AND METHODS

(71) Applicant: Bethany Valente, Wheaton, IL (US)

(72) Inventor: Bethany Valente, Wheaton, IL (US)

( * ) Notice: Subject to any disclaimer, the term of this patent is extended or adjusted under 35 U.S.C. 154(b) by 4 days.

(21) Appl. No.: 18/827,474

(22) Filed: Sep. 6, 2024

(65) Prior Publication Data

US 2025/0087314 A1 Mar. 13, 2025

Related U.S. Application Data

(60) Provisional application No. 63/581,655, filed on Sep. 9, 2023.

(51) Int. Cl.

| | |
|---|---|
| ***G16H 10/20*** | (2018.01) |
| ***G06F 3/16*** | (2006.01) |
| ***G10L 15/08*** | (2006.01) |
| ***H04W 4/02*** | (2018.01) |

(52) U.S. Cl.

CPC ............. *G16H 10/20* (2018.01); *G06F 3/167* (2013.01); *G10L 15/08* (2013.01); *H04W 4/025* (2013.01); *G10L 2015/088* (2013.01)

(58) Field of Classification Search

None

See application file for complete search history.

(56) References Cited

U.S. PATENT DOCUMENTS

| | | | | |
|---|---|---|---|---|
| 10,878,691 | B1 | 12/2020 | Mclendon et al. | |
| 2015/0220694 | A1 | 8/2015 | Abbott et al. | |
| 2016/0004831 | A1* | 1/2016 | Carlson | G16H 10/20 705/2 |
| 2018/0000425 | A1* | 1/2018 | Hernacki | A61B 5/746 |
| 2018/0277251 | A1 | 9/2018 | Karim et al. | |
| 2020/0013509 | A1* | 1/2020 | Matharu | G16H 20/70 |
| 2021/0142897 | A1 | 5/2021 | Mclendon et al. | |
| 2022/0110591 | A1* | 4/2022 | Peres | A61B 5/12 |
| 2024/0105334 | A1* | 3/2024 | Aronovich | G16H 50/30 |

FOREIGN PATENT DOCUMENTS

| | | | | |
|---|---|---|---|---|
| WO | WO-2016/193879 A1 | 12/2016 | | |
| WO | WO-2018/051103 A1 | 3/2018 | | |
| WO | WO-2020234604 A1 * | 11/2020 | | G16H 40/63 |

OTHER PUBLICATIONS

"Alexa Migraine Buddy" Nov. 7, 2020, last accessed Sep. 6, 2025, available at: https://web.archive.org/web/20201107234150/https://www.amazon.com/Healint-Migraine-Buddy/dp/B07CG499WF (Year: 2020).*

* cited by examiner

*Primary Examiner* — Katherine Kolosowski-Gager

(74) *Attorney, Agent, or Firm* — FOLEY & LARDNER LLP

(57) ABSTRACT

A mobile device for tracking migraine symptoms can include a processing circuit comprising one or more processors and one or more computer-readable storage media having instructions stored thereon executable by the one or more processors; an input device configured to be activated by a user and, responsive to activation, cause the processing circuit to begin a data collection process by prompting the user with one or more predetermined prompts; and one or more audio devices configured to output the one or more predetermined prompts to the user; and receive one or more responses to the one or more predetermined prompts from the user.

17 Claims, 5 Drawing Sheets

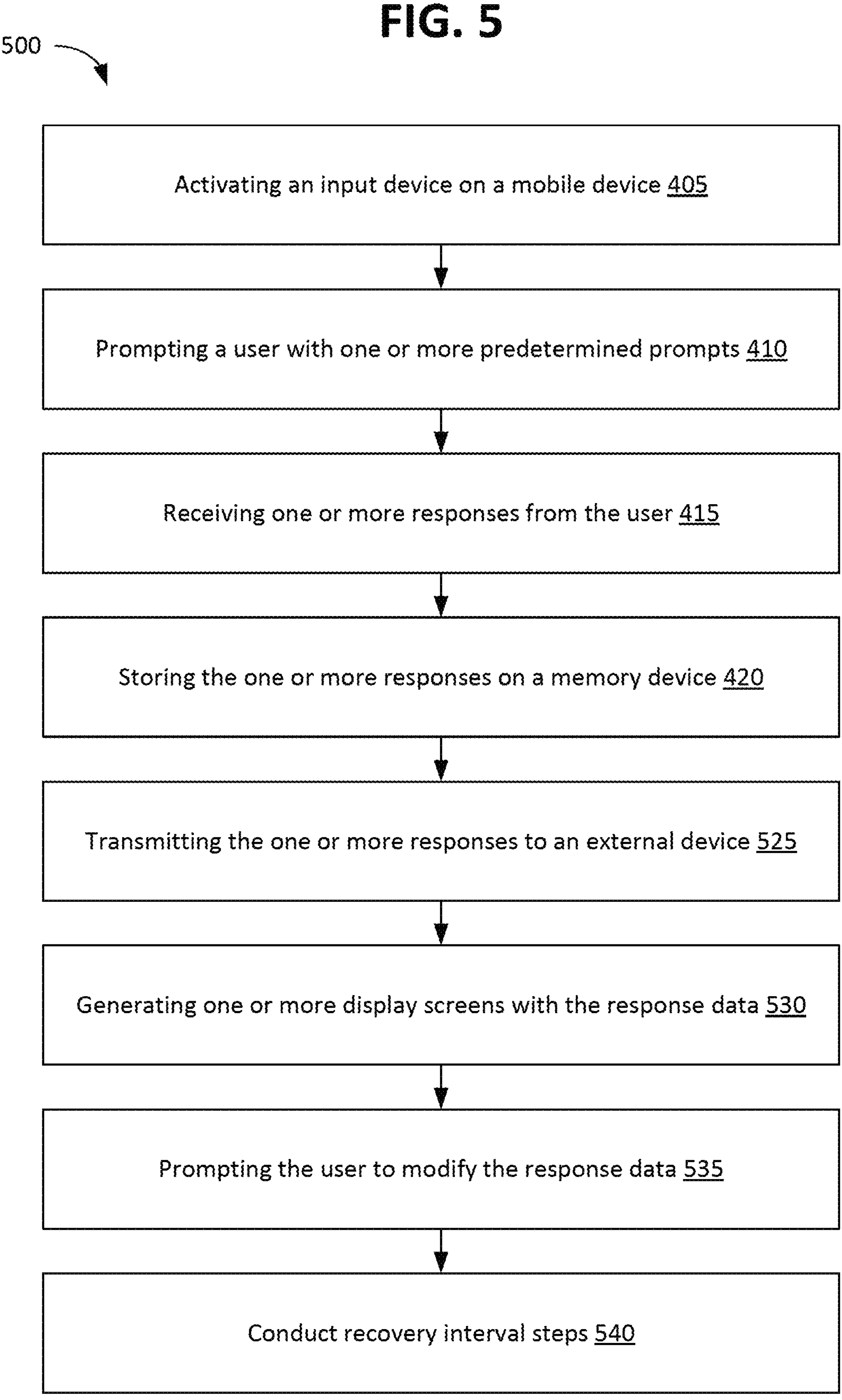
FIG. 5
500
Activating an input device on a mobile device 405
Prompting a user with one or more predetermined prompts 410
Receiving one or more responses from the user 415
Storing the one or more responses on a memory device 420
Transmitting the one or more responses to an external device 525
Generating one or more display screens with the response data 530
Prompting the user to modify the response data 535
Conduct recovery interval steps 540

MIGRAINE SYMPTOM AND MEDICATION TRACKING DEVICE FOR USE IN SYSTEMS AND METHODS

CROSS REFERENCE TO RELATED APPLICATION(S)

This application claims the benefit of and priority to U.S. Provisional Patent Application No. 63/581,655, filed Sep. 9, 2023, the disclosure of which is hereby incorporated by reference in its entirety for all purposes.

TECHNOLOGY FIELD

The present disclosure relates to devices, systems, and associated methods for tracking symptoms and medication use relating to migraines.

BACKGROUND

When managing a medical condition with symptoms that are episodic in nature, patients are often asked by their doctor to track their symptoms and medications taken during episodes. This practice allows doctors to assess whether the patient's current treatment plan is effective or if changes to the patient's medication regimen and/or habits need to be made. Sometimes though, symptoms of medical conditions can inhibit symptom tracking.

Some solutions have tried using applications on mobile devices, such as smartphones or tablets, so that the patient can quickly add their symptoms and/or add to them later. However, there are problems with existing systems because screen-based devices running applications tend to exacerbate symptoms, such as vertigo, seizures, nausea, etc. Furthermore, such symptoms may cause the patient to defer symptom tracking to a later time, particularly since it's easy to do and/or convenient. The current solutions, thus, can lead to inaccurate patient data.

Therefore, there is a need in the field for an improved migraine symptom and medication tracking device, as well as a system and a method incorporating such a device.

SUMMARY

At least one embodiment described herein relates to a mobile device for tracking migraine symptoms. The mobile device may include a processing circuit. The processing circuit may include one or more processors and one or more computer-readable storage media having instructions. The mobile device may also include an input device that is configured to be activated by a user and, responsive to activation, cause the processing unit to begin a data collection process by prompting the user with one or more predetermined prompts. The mobile device may also include one or more audio devices configured to output the one or more predetermined prompts to the user and receive one or more responses to the one or more predetermined prompts from the user. The processing circuit may be configured to store the responses to the one or more predetermined prompts in the one or more computer-readable storage media.

In some embodiments, the input device of the mobile device comprises one or more buttons. The one or more buttons may be further configured to be activated by the user to provide the one or more responses in response to the one or more predetermined questions. The one or more buttons may comprise a first button configured to detect a set of one or more presses, and the processing circuit may be configured to determine a first response of the one or more responses to be a first predetermined response based on the set of presses including a first number of presses and determine the first response to be a second predetermined response different from the first predetermined response based on the set of presses including a second number of presses different from the first number of presses. The one or more buttons may comprise a first button and a second button and the processing circuit may be configured to determine a first response of the one or more responses to be a first predetermined response based on activation of the first button and determine the first response to be a second predetermined response different from the first predetermined response based on activation of the second button.

In some embodiments, the mobile device may further comprise a communications interface configured to communicate with an external device. The processing circuit may be configured to transmit data based on the one or more responses to the external device using the communications interface.

In some embodiments, the mobile device may further comprise a communications interface configured to communicate with an external device and location determination circuitry configured to determine a location of the mobile device. The processing circuit may be configured to transmit the location of the mobile device to the external device using the communications interface.

In some embodiments, the mobile device may comprise one or more audio devices that include a microphone. The microphone may comprise the input device and the processing circuit may be configured to initiate the data collection process responsive to the microphone detecting a predetermined set of one or more activation keywords.

In some embodiments, the mobile device may comprise one or more audio devices that may include a speaker.

In some embodiments, the mobile device may be devoid of a visual display device.

In some embodiments, a system for tracking migraine symptoms is described herein. The system may comprise a mobile device. The mobile device may comprise a processing circuit comprising one or more first processors and a first set of one or more computer-readable storage media having instructions stored thereon executable by the one or more processors. The mobile device may comprise a first communications interface configured to communicate over a network, wherein the processing circuit is configured to transmit data using the first communications interface. The mobile device may comprise an input device configured to be activated by a user and, responsive to activation, cause the processing circuit to begin a data collection process by prompting the user with one or more predetermined prompts. The mobile device may comprise one or more audio devices configured to output the one or more predetermined prompts to the user and receive one or more responses to the one or more predetermined prompts from the user. The system may comprise a second set of one or more non-transitory computer-readable storage media having instructions stored thereon that, when executed by one or more second processors, cause the one or more second processors to receive, from the mobile device, data corresponding to the one or more responses; generate one or more display screens, wherein the one or more display screens contain one or more pieces of the data; and prompt, on the one or more display screens, the user to at least one of confirm or modify the one or more pieces of the data.

In some embodiments, the instructions on the second one or more non-transitory computer-readable storage media may further cause the one or more processors to: prompt the user, after a predetermined recovery interval, with one or more predetermined recovery prompts; receive, in response to the one or more predetermined recovery prompts, one or more recovery responses; and store the one or more recovery responses received in the first one or more computer-readable storage media of the mobile device.

In some embodiments, a method for tracking migraine symptoms is described herein. The method may comprise a step of activating an input device on a mobile device, wherein activating the input device begins a data collection process. The method may comprise a step of prompting a user, from one or more audio devices of the mobile device, with one or more predetermined prompts during the data collection process. The method may comprise a step of receiving, in response to the one or more predetermined prompts, one or more responses. The method may comprise a step of storing the one or more responses received in a first one or more computer-readable storage media of the mobile device.

In some embodiments, the one or more responses may be received by the one or more audio devices of the mobile device.

In some embodiments, the input device of the mobile device may comprise one or more buttons. The one or more response may be received by activation of the one or more buttons.

In some embodiments, the method may comprise a step of transmitting the one or more responses to a second one or more non-transitory computer-readable storage media. The method may comprise a step of generating, by the second one or more non-transitory computer-readable storage media, one or more display screens, wherein the one or more display screens contain data corresponding to the one or more responses. The method may comprise a step of prompting, on the one or more display screens, the user to modify the one or more pieces of the data.

In some embodiments, the method may comprise a step of transmitting a location of the mobile device to a second one or more non-transitory computer-readable storage media. The method may comprise a step of alerting, by the second one or more non-transitory computer-readable storage media, one or more predetermined contacts.

In some embodiments, the method may comprise a step of prompting the user, after a predetermined recovery interval, with one or more predetermined recovery prompts. The method may comprise a step of receiving, in response to the one or more predetermined recovery prompts, one or more recovery responses. The method may comprise a step of storing the one or more recovery responses received in the first one or more computer-readable storage media of the mobile device.

BRIEF DESCRIPTION OF THE DRAWINGS

Further features, characteristics, and advantages of the present disclosure will become apparent to a person of ordinary skill in the art from the following detailed description of embodiments of the present disclosure, made with reference to the drawings annexed, in which like reference characters refer to like elements.

FIG. 5 is a flowchart depicting a method for tracking migraine symptoms, according to some embodiments.

DETAILED DESCRIPTION

Figure 1:
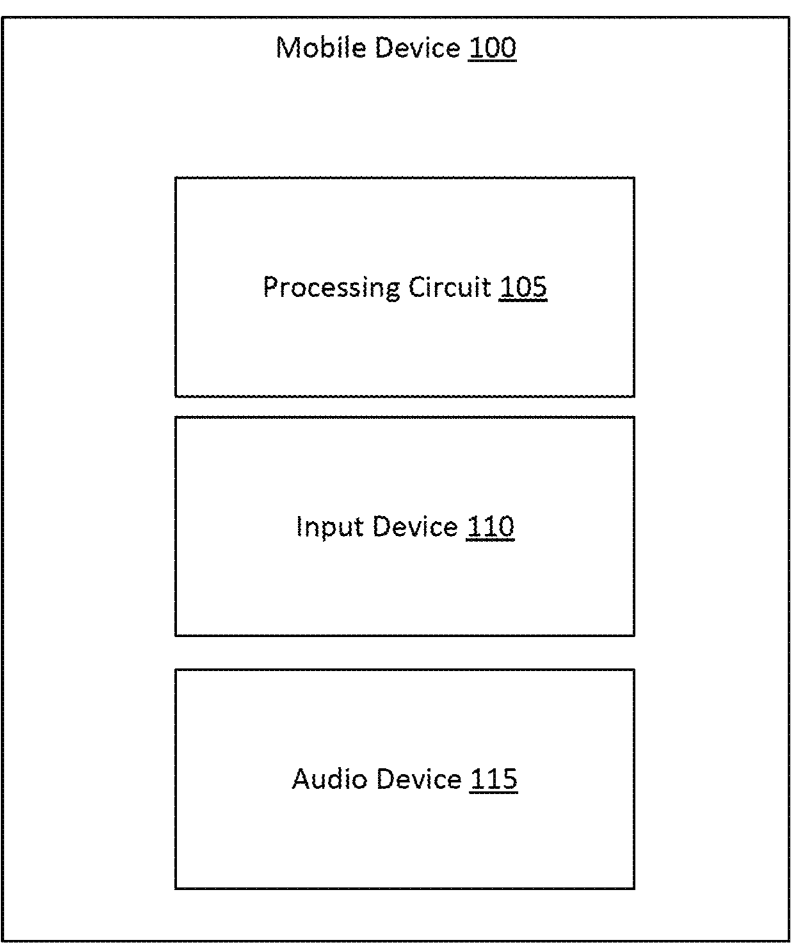
FIG. 1 is a block diagram depicting a migraine symptom tracking device, according to some embodiments.

FIG. 1 depicts a block diagram of a mobile device 100, according to some embodiments. The mobile device 100 may be used to track symptoms and/or medication use during episodes relating to one or more medical conditions (e.g., migraines, seizures, etc.). In some embodiments, the mobile device 100 may be a handheld device. In some embodiments, the mobile device 100 may be completely devoid of a display (i.e., lacking a screen, display, or any other visual component). In some embodiments, the mobile device 100 may include one or more connectors (e.g., keychain, magnet, etc.). In some embodiments, the mobile device 100 may include a processing circuit 105, an input device 110, and/or an audio device 115.

In some embodiments, the mobile device 100 may include the processing circuit 105. In some embodiments, the processing circuit 105 may include one or more processors, one or more computer-readable storage media, one or more memory devices, and/or one or more sets of instructions. In some embodiments, the processing circuit 105 may monitor interactions with the mobile device 100 (e.g., button presses, user input, etc.). For example, a user may interact with a button that causes a data collection process to begin, where the processing circuit 105 prompts the user with one or more predetermined prompts from memory. In some embodiments, one or more predetermined prompts may reside on the mobile device 100 (e.g., stored in a database) and may include prompts such as: did you take medication; do you have a migraine aura; are you experiencing nausea; etc. In some embodiments, the predetermined prompts may be in the form of questions, phrases, and/or groupings of words. In some embodiments, the predetermined prompts may be in the form of "yes-or-no" questions.

In some embodiments, the processing circuit 105 may be responsible for outputting one or more predetermined prompts to solicit a response. In some embodiments, the processing circuit 105 may receive one or more responses to the outputted prompts. For example, a user may respond to one or more prompts with the input device 110. In some embodiments, the processing circuit 105 may store the data associated with one or more responses (e.g., store the user's responses in a database on the mobile device 100).

In some embodiments, the processing circuit 105 may be programmed to carry out one or more recovery interval steps. In some embodiments, the processing circuit 105 may be programmed to prompt the user with one or more predetermined recovery prompts after a certain amount of time has passed (i.e., the recovery interval). For example, if the recovery interval is five hours, then after five hours have passed since the data collection process, the processing circuit 105 may prompt the user with one or more predetermined recovery prompts such as: do you still have a headache; are any symptoms remaining; would you like to begin the data collection process again; etc. In some embodiments, the processing circuit 105 may receive one or more responses to the outputted recovery prompts. In some embodiments, the processing circuit 105 may store the data associated with the recovery prompt responses.

In some embodiments, the mobile device 100 may include the input device 110. In some embodiments, the input device 110 may include one or more devices corresponding to one or more forms of input (e.g., audio, touch, etc.). In some embodiments, the input device 110 may be activated by a user. In some embodiments, activation of the input device 110 may cause the processing circuit 105 to begin a data collection process. For example, a user experiencing a migraine episode may activate the input device 110 to cause the processing circuit 105 of the mobile device 100 to begin symptom and/or medication use tracking by prompting the user with one or more predetermined prompts.

In some embodiments, the input device 110 may include one or more buttons. In some embodiments, the input device 110 may use one or more buttons to receive user input. For example, a user may press a button of the input device 110 to begin a data collection process. In another example, a user may press and hold (e.g., for 3 seconds) a button of the input device 110 to begin a data collection process. In yet another example, the input device 110 may include multiple buttons corresponding to different responses a user might wish to convey (e.g., a button may correspond to an affirmative response, a button may correspond to a negative response, etc.), where the processing circuit 105 is configured to determine which input button corresponds to which response. In some embodiments, the input device 110 may include one button, where the processing circuit 105 is configured to differentiate actions, activations, and/or responses based on interactions with the button. For example, holding the button for multiple seconds may correspond to initiating a data collection process, pressing the button once may correspond to an affirmative response, pressing the button twice may correspond to a negative response, etc.

In some embodiments, the input device 110 may include an audio input device, such as a microphone. In some embodiments, the input device 110 may cause the processing circuit 105 to initiate a data collection process based on one or more activation keywords received via an audio input device. For example, a user may speak into a microphone of the device words and/or phrases which begin a data collection process, such as "migraine attack," "migraine symptoms," "migraine help," etc. In some embodiments, the input device 110 may include a microphone that receives responses from a user to outputted prompts. For example, a predetermined prompt may ask a user, "are you experience head pain?" and the user may respond orally with "yes" or "no," where the response is taken in by a microphone serving as the input device 110.

In some embodiments, the mobile device 100 may include the audio input device 115. In some embodiments, the audio device 115 may include one or more audio devices. In some embodiments, the audio device 115 may include one or more speakers, one or more microphones, and/or one or more other audio elements, which may be integrated within or connected to the mobile device 100. In some embodiments, the audio device 115 may be configured to output information to a user (e.g., data collection prompts, questions, battery level, volume level, etc.). In some embodiments, the audio device 115 may be configured to receive input. For example, a user may respond orally to one or more predetermined prompts during a data collection process, and the audio device 115 may receive the responses, serving in a role similar to the input device 110. In some embodiments, the audio device 115 may include one or more buttons to adjust audio levels (e.g., a button to increase the output sound level, a button to decrease the output sound level, etc.).

Figure 2:
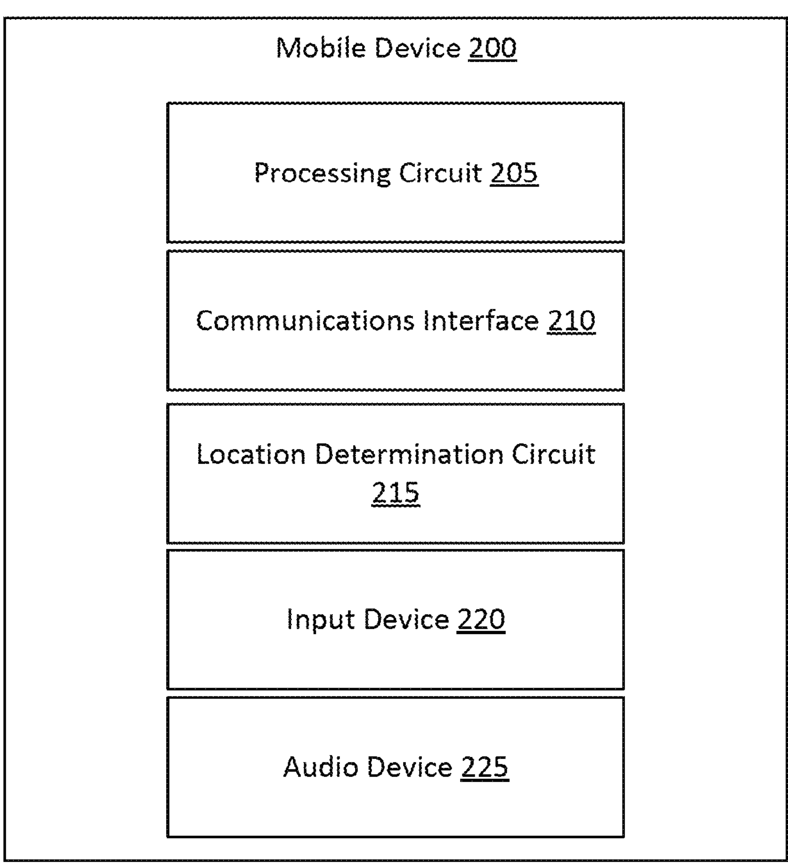
FIG. 2 is a block diagram depicting a migraine symptom tracking device, according to some embodiments.

FIG. 2 depicts a block diagram of a mobile device 200, according to some embodiments. In some embodiments, the mobile device 200 may be similar to the mobile device 100 depicted in FIG. 1. The mobile device 200 may be used to track symptoms and/or medication use during episodes relating to one or more medical conditions (e.g., migraines, seizures, etc.). In some embodiments, the mobile device 200 may be a handheld device. In some embodiments, the mobile device 200 may be completely devoid of a display (i.e., lacking a screen, display, or any other visual component). In some embodiments, the mobile device 200 may include one or more connectors (e.g., keychain, magnet, etc.). In some embodiments, the mobile device 200 may include a processing circuit 205, a communications interface 210, a location determination circuit 215, an input device 220, and/or an audio device 225.

In some embodiments, the mobile device 200 may include a processing circuit 205. The processing circuit 205 of the mobile device 200 is substantially similar to the processing circuit 105 of the mobile device 100 depicted in FIG. 1 and described above.

In some embodiments, the mobile device 200 may include a communications interface 210. In some embodiments, the communications interface 210 may include components for a USB interface, Ethernet, wired connections, wireless connections (e.g., Wi-Fi, LAN, Bluetooth, etc.), etc. In some embodiments, the communications interface 210 may allow the mobile device 200 to receive data. For example, the mobile device 200 may receive one or more predetermined prompts from an external device and store those in memory so that the processing circuit 205 can access them for data collection purposes. In some embodiments, the communications interface 210 may allow the mobile device 200 to transfer data. For example, after one or more response have been received by the processing circuit 205, the processing circuit 205 may transmit the responses to one or more other devices (e.g., computer, server, tablet, smartphone, external database, etc.), using the communications interface 210. In some embodiments, data transfer via the communications interface 210 may occur after the entire data collection process has completed. In some embodiments, data transfer via the communications interface 210 may occur as each response is received during the data collection process.

In some embodiments, the mobile device 200 may include a location determination circuit 215. In some embodiments, the location determination circuit 215 may be configured with one or more processors, one or more memory devices, and/or one or more instructions to determine the location of the mobile device 200. In some embodiments, the location determination circuit 215 may use various Global Positioning System (GPS) services to determine the location and/or position data corresponding to the mobile device 200. In some embodiments, the location determination circuit 215 may transmit, with the communications interface 210, the mobile device 200 location data to one or more external devices. For example, a user's location data may be sent to an external computing device for data storage to help track where symptoms occur/worsen. In another example, the location data of a user may be sent to one or more contacts (e.g., emergency contacts, medical authorities, first responders, physicians, etc.). In some embodiments, the location data may be transmitted after a response is received to one or more predetermined prompts. For example, if a prompt says, "would you like to send your location data to your emergency contact" and the user responds affirmatively, then the location determination circuit 215 may transmit the data.

In some embodiments, the mobile device 200 may include an input device 220. The input device 220 of the mobile device 200 is substantially similar to the input device 110 of the mobile device 100 depicted in FIG. 1 and described above.

In some embodiments, the mobile device 200 may include an audio device 225. The audio device 225 of the mobile device 200 is substantially similar to the audio device 115 of the mobile device 100 depicted in FIG. 1 and described above.

Figure 3:
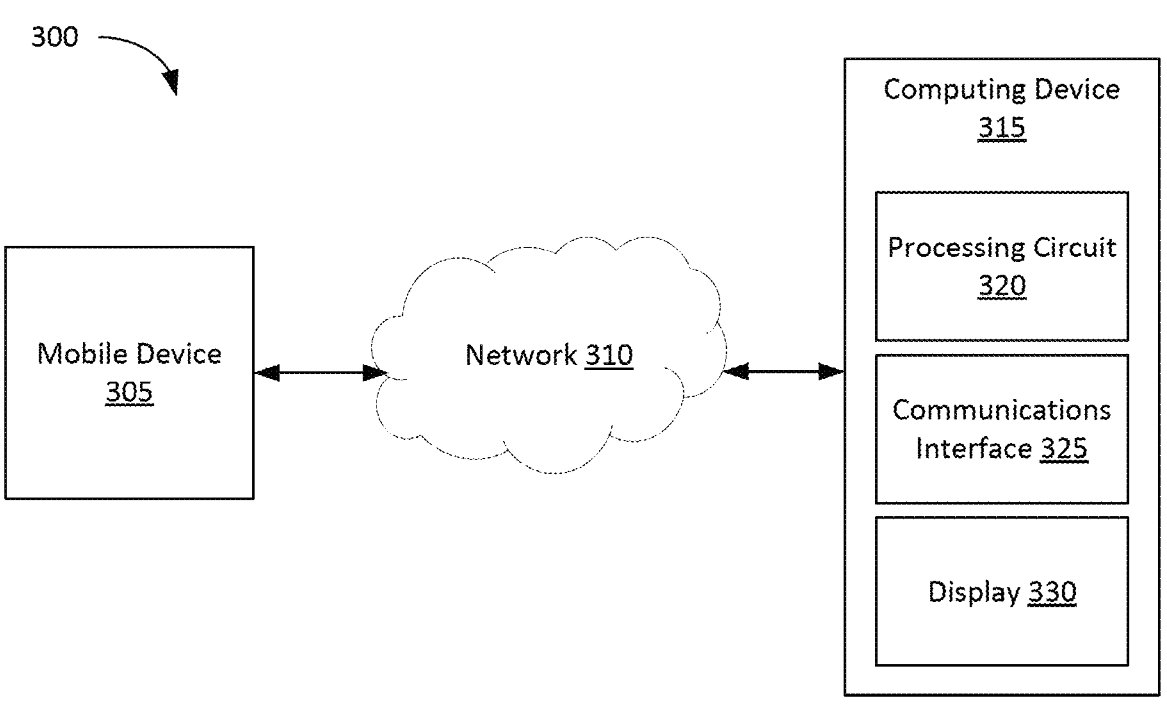
FIG. 3 is a block diagram depicting a system for tracking migraine symptoms, according to some embodiments.

FIG. 3 depicts a block diagram of a system 300, according to some embodiments. In some embodiments, the system 300 may be used for tracking symptoms of user experiencing a migraine. In some embodiments, the system 300 may include a mobile device 305, a network 310, and/or a computing device 315. In some embodiments, the components of the system 300 may communicate with one another over the network 310. For example, the mobile device 305 may communicate over the network 310 with the computing device 315 to receive/transmit data pertaining to tracking migraine symptoms.

In some embodiments, the system 300 may include a mobile device 305. In some embodiments, the mobile device 305 may be a version of the mobile device 100 depicted in FIG. 1, a version of the mobile device 200 depicted in FIG. 2, or a similar device. In some embodiments, the mobile device 305 may be devoid of any visual display device (e.g., screen, display, etc.). In some embodiments, the mobile device 305 may receive input through various input devices (e.g., buttons, microphones, etc.). In some embodiments, the mobile device 305 may solicit input by outputting various prompts (e.g., questions, phrases, yes-or-no questions, etc.). In some embodiments, the mobile device 305 may output data with one or more audio devices (e.g., speakers). In some embodiments, the mobile device 305 may store data for later use. In some embodiments, the mobile device 305 may include a communications interface in order to transmit data. In some embodiments, the mobile device 305 may transmit data to another device. For example, the mobile device 305 may transmit data received in response to one or more prompts over the network 310 to a computing device 315.

In some embodiments, the system 300 may include a network 310. In some embodiments, the network 310 may facilitate communication between various devices. In some embodiments, the network 310 may be the Internet, a WAN, a LAN, a cellular network, etc.

In some embodiments, the system 300 may include a computing device 315. In some embodiments, the computing device 315 may include at least one processing circuit 320, a communications interface 325, and/or at least one display 330. In some embodiments, the computing device 315 may be a computer (e.g., desktop computer, laptop, etc.). In some embodiments, the computing device may be a handheld device (e.g., smartphone, cellphone, tablet, etc.). In some embodiments, the computing device 315 may communicate over the network 310. In some embodiments, the computing device 315 may receive data (e.g., response data to one or more prompts, location data, etc.) from the mobile device 305 over the network 310. In some embodiments, the computing device 315 may transmit data (e.g., one or more prompts, one or more user created prompts, etc.) to the mobile device 305 over the network 310.

In some embodiments, the computing device 315 may include a processing circuit 320 to perform one or more instructions stored in a memory device. For example, the processing circuit 320 may be configured to receive data from the mobile device 305 by interacting with the communications interface 325. In some embodiments, the processing circuit 320 may generate one or more display screens on the display 330. In some embodiments, the display 330 may provide information visually to a user regarding one or more pieces of data (e.g., responses to prompts, previous user data, user-created prompts, etc.). For example, the display 330 may depict a set of prompts with answers that the user gave on the mobile device 305 and that the computing device 315 received over the network 310. In some embodiments, the processing circuit 320 may prompt a user to confirm and/or modify one or more elements depicted on the display 330. For example, a user may have responded affirmatively during a data collection process on the mobile device 305 when they meant to respond in the negative. The processing circuit 320 of the computing device 315 may allow for the user to change such a response, by manipulating the data shown on the display 330, to reflect the more accurate answer.

Figure 4:
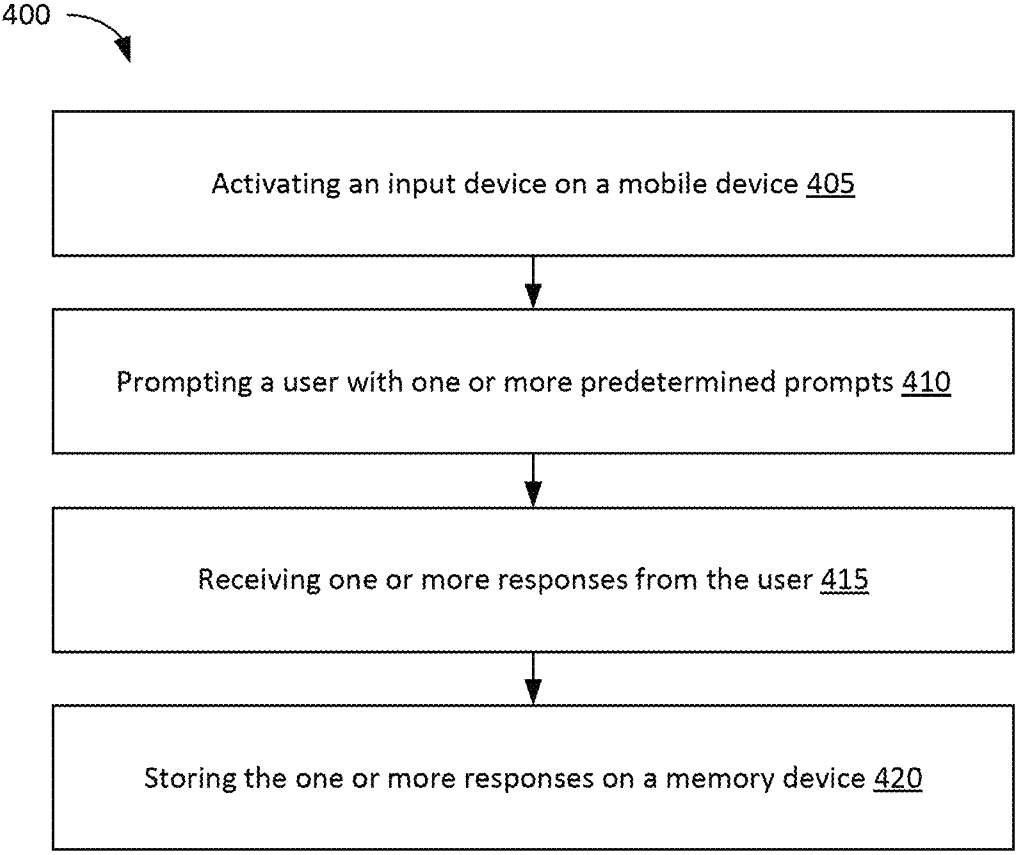
FIG. 4 is a flowchart depicting a method for tracking migraine symptoms, according to some embodiments.

FIG. 4 depicts a flowchart of a method 400 for tracking migraine symptoms, according to some embodiments. In some embodiments, the method 400 and/or one or more steps thereof may be performed and/or executed by at least one of the various systems, devices, and/or components described herein. For example, the steps of method 400 may be performed by the mobile device 305 and the computing device 315 of the system 300. In some embodiments, the method 400 and/or one or more steps thereof may be replicated, reproduced, repeated, separated, modified, changed, and/or altered. For example, a given step of the method 400 may be performed multiple times.

In some embodiments, at step 405, an input device on a mobile device may be activated. For example, the input device 110 of the mobile device 100 or the input device 220 of the mobile device 200 may be interacted with (e.g., button press, keyword activation, etc.). In some embodiments, at step 405, activating the input device may cause the mobile device to begin a data collection process, where the data collection process entails prompting the user with various prompts (e.g., questions, phrases, etc.) related to a migraine episode.

In some embodiments, at step 410, a user may be prompted with one or more predetermined prompts. For example, the mobile device 305 may output one or more predetermined prompts and await user response through an input device. In some embodiments, at step 410, the one or more predetermined prompts may be stored directly on the mobile device 305. In some embodiments, at step 410, the mobile device 305 may receive one or more predetermined prompts from the computing device 315 over the network 310. In some embodiments, at step 410, the mobile device 305 may request (i.e., GET request) one or more predetermined prompts from the computing device 315 each time the data collection process is initiated. In some embodiments, at step 410, the mobile device 305 may request (i.e., GET request) from the computing device 315 each predetermined prompt individually as the data collection process continues (i.e., after each response is received).

In some embodiments, at step 415, a migraine tracking device may receive one or more responses from a user. For example, the mobile device 305 may receive user input via an input device corresponding to responses to the various predetermined prompts in step 410. In some embodiments, at step 415, the mobile device 305 may receive user input through one or more buttons. In some embodiments, at step 415, the mobile device 305 may receive user input orally, for example, through one or more microphones.

In some embodiments, at step 420, a migraine tracking device may store the one or more responses on a memory device. For example, the mobile device 305 may store the user responses on a memory component in the mobile device 305. In some embodiments, at step 420, the mobile device 305 may store the data for temporary use (e.g., one day, one week, one month, etc.) or for an unbounded period of time. For example, the mobile device 305 may store the data associated with a user's responses until the data is transmitted to another device for further processing.

FIG. 5 depicts a flowchart of a method 500 for tracking migraine symptoms, according to some embodiments. In some embodiments, the method 500 and/or one or more steps thereof may be performed and/or executed by at least one of the various systems, devices, and/or components described herein. For example, the steps of method 500 may be performed by the mobile device 305 and the computing device 315 of the system 300. In some embodiments, the method 500 and/or one or more steps thereof may be replicated, reproduced, repeated, separated, modified, changed, and/or altered. For example, a given step of the method 500 may be performed multiple times. In some embodiments, the method 500 may contain one or more steps of the method 400 depicted in FIG. 4, including step 405, step 410, step 415, and/or step 420.

In some embodiments, at step 525, a migraine tracking device transmits one or more responses to an external device. For example, the mobile device 305 may receive user input responding to one or more predetermined prompts and then transmit that data (e.g., over the network 310) to an external device, such as the computing device 315. In some embodiments, at step 525, the mobile device 305 may transmit the data to multiple external devices concurrently. In some embodiments, at step 525, the mobile device 305 may transmit data corresponding to each individual response as it is received through an input device. For example, each time a user answers a predetermined prompt, the mobile device 305 transmits the response to the computing device 315. In some embodiments, at step 525, the mobile device 305 transmits all the data after the data collection process has ended.

In some embodiments, at step 530, a computing device may generate one or more display screens with data corresponding to one or more responses. For example, the computing device 315 may, after receiving data corresponding to a user's responses during the data collection process, generate a display screen to provide a visual representation of the data to the user. In some embodiments, at step 530, the one or more display screens may be generated with one or more predetermined prompts and their corresponding one or more responses. In some embodiments, at step 530, the one or more display screens may have navigation controls so that a user may move between different screens. For example, each screen may display one predetermined prompt and its corresponding response, so there may be a display screen for each prompt-response pair, meaning there may be navigation tools to change the currently displayed screen.

In some embodiments, at step 535, a computing device may prompt a user to modify the response data. For example, the computing device 315 may ask the user to modify a response they had given during the data collection process. In another example, the computing device 315 may ask the user to confirm a response they had given during the data collection process. In some embodiments, at step 535, the user may modify the data by selecting between predetermined answers (e.g., switch from "yes" to "no"). In some embodiments, at step 535, the user may modify the data by writing a free-text response to the predetermined prompt.

In some embodiments, at step 540, a migraine tracking device may conduct one or more recovery interval steps. For example, the mobile device 305 may be programmed to prompt the user again after a set amount of time has passed (i.e., the recovery interval) after the user has initiated a data collection process. In some embodiments, at step 540, the mobile device 305 prompts the user with one or more predetermined recovery prompts. In some embodiments, at step 540, a recovery interval step may be receiving responses to one or more predetermined recovery prompts. For example, the mobile device 305 may receive responses to the recovery prompts in a similar fashion as the responses to the prompts during the data collection process. In some embodiments, at step 540, a recovery interval step may be storing and/or transmitting the data associated with responses to one or more predetermined recovery prompts. For example, the mobile device 305 may store and/or transmit the response to the recovery prompts in a similar fashion as the responses to the prompts during the data collection process.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general-purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with processing circuits employing rule-based logic and other logic to accomplish the various connection steps, processing steps, comparison steps and decision steps.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be any of X; Y; Z; X and Y; X and Z; Y and Z; or X, Y, and Z. Thus, such conjunctive language is not generally intended to imply that certain embodiments require at least one of X, at least one of Y, and at least one of Z to each be present.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed:

1. A mobile device for tracking migraine symptoms, the mobile device comprising:

a processing circuit comprising one or more processors and one or more computer-readable storage media having instructions stored thereon executable by the one or more processors;

an input device devoid of a display configured to be activated by a user during a migraine episode and, responsive to activation, cause the processing circuit to begin a data collection process by prompting the user with one or more first predetermined prompts; and one or more audio devices configured to:

output the one or more first predetermined prompts to the user in response to the activation;

receive one or more first responses to the one or more first predetermined prompts from the user;

output one or more second predetermined prompts to the user after a recovery interval has passed, the one or more second predetermined prompts comprising one or more recovery prompts regarding the migraine episode; and receive one or more second responses to the one or more second predetermined prompts from the user;

wherein the processing circuit is configured to store the one or more first responses and the one or more second responses in the one or more computer-readable storage media.

2. The device of claim 1, wherein the input device comprises one or more buttons.

3. The device of claim 2, wherein the one or more buttons are further configured to be activated by the user to provide the one or more first responses in response to the one or more first predetermined prompts.

4. The device of claim 3, wherein the one or more buttons comprise a first button configured to detect a set of one or more presses, and wherein the processing circuit is configured to:

determine a first response of the one or more first responses to be a first predetermined response based on the set of presses including a first number of presses; and determine the first response to be a second predetermined response different from the first predetermined response based on the set of presses including a second number of presses different from the first number of presses.

5. The device of claim 3, wherein the one or more buttons comprise a first button and a second button, and wherein the processing circuit is configured to:

determine a first response of the one or more first responses to be a first predetermined response based on activation of the first button; and determine the first response to be a second predetermined response different from the first predetermined response based on activation of the second button.

6. The device of claim 1, further comprising a communications interface configured to communicate with an external device, wherein the processing circuit is configured to transmit data based on the one or more first responses and the one or more second responses to the external device using the communications interface.

7. The device of claim 1, further comprising a communications interface configured to communicate with an external device and location determination circuitry configured to determine a location of the mobile device, wherein the processing circuit is configured to transmit the location of the mobile device to the external device using the communications interface.

8. The device of claim 1, wherein the one or more audio devices comprises a microphone.

9. The device of claim 8, wherein the microphone comprises the input device and the processing circuit is configured to initiate the data collection process responsive to the microphone detecting a predetermined set of one or more activation keywords.

10. The device of claim 1, wherein the one or more audio devices comprises a speaker.

11. A system for tracking migraine symptoms, the system comprising:

a mobile device comprising:

a processing circuit comprising one or more first processors and a first set of one or more computer-readable storage media having instructions stored thereon executable by the one or more first processors;

a first communications interface configured to communicate over a network, wherein the processing circuit is configured to transmit data using the first communications interface;

an input device devoid of a display and configured to be activated by a user during a migraine episode and, responsive to activation, cause the processing circuit to begin a data collection process by prompting the user with one or more first predetermined prompts; and one or more audio devices configured to:

output the one or more first predetermined prompts to the user;

receive one or more first responses to the one or more first predetermined prompts from the user;

output one or more second predetermined prompts to the user after a recovery interval has passed, the one or more second predetermined prompts comprising one or more recovery prompts regarding the migraine episode; and receive one or more second responses to the one or more second predetermined prompts from the user;

a second set of one or more non-transitory computer-readable storage media having instructions stored thereon that, when executed by one or more second processors, cause the one or more second processors to:

receive, from the mobile device, data corresponding to the one or more first responses and the one or more second responses;

generate one or more display screens on a display of the mobile device separate from the input device, wherein the one or more display screens contain one or more pieces of the data; and prompt, on the one or more display screens, the user to at least one of confirm or modify the one or more pieces of the data.

12. A method for tracking migraine symptoms, the method comprising:

activating an input device on a mobile device during a migraine episode, the input device devoid of a display, wherein activating the input device begins a data collection process;

in response to the activation, prompting a user, from one or more audio devices of the mobile device, with one or more first predetermined prompts during the data collection process;

receiving, in response to the one or more first predetermined prompts, one or more first responses;

prompting the user, from the one or more audio devices during the data collection process after a recovery interval has passed, with one or more second predetermined prompts comprising one or more recovery prompts regarding the migraine episode;

receiving, in response to the one or more second predetermined prompts, one or more second responses; and storing the one or more first responses and the one or more second responses received in a first one or more computer-readable storage media of the mobile device.

13. The method of claim 12, wherein the one or more first responses and the one or more second responses are received by the one or more audio devices of the mobile device.

14. The method of claim 12, wherein the input device of the mobile device comprises one or more buttons.

15. The method of claim 14, wherein the one or more first responses are received by activation of the one or more buttons.

16. The method of claim 12, further comprising:

transmitting the one or more first responses to a second one or more non-transitory computer-readable storage media;

generating, by the second one or more non-transitory computer-readable storage media, one or more display screens on a display of the mobile device separate from the input device, wherein the one or more display screens contain data corresponding to the one or more responses; and prompting, on the one or more display screens, the user to modify one or more pieces of the data.

17. The method of claim 12, further comprising:

transmitting a location of the mobile device to a second one or more non-transitory computer-readable storage media; and alerting, by the second one or more non-transitory computer-readable storage media, one or more predetermined contacts.

* * * * *